(12) United States Patent
Wu et al.

(10) Patent No.: US 8,278,500 B2
(45) Date of Patent: Oct. 2, 2012

(54) SWITCHGRASS CULTIVAR

(75) Inventors: Yanqi Wu, Stillwater, OK (US); Charles M. Taliaferro, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 504 days.

(21) Appl. No.: 12/466,605

(22) Filed: May 15, 2009

(65) Prior Publication Data

US 2009/0300977 A1    Dec. 10, 2009

Related U.S. Application Data

(60) Provisional application No. 61/053,530, filed on May 15, 2008.

(51) Int. Cl.
*A01H 1/04* (2006.01)
*A01H 4/00* (2006.01)
*A01H 5/04* (2006.01)

(52) U.S. Cl. .................. 800/266; 800/260; 800/268

(58) Field of Classification Search .................. 800/260, 800/266, 268
See application file for complete search history.

(56) References Cited

U.S. PATENT DOCUMENTS

| | | | |
|---|---|---|---|
| 6,407,319 | B1 | 6/2002 | Rose-Fricker et al. |
| 6,677,507 | B2 | 1/2004 | De Bruijn |
| 7,511,205 | B1 | 3/2009 | Noble, Jr. |
| 7,525,028 | B2 | 4/2009 | Jenkinson |

OTHER PUBLICATIONS

Taliaferro, C. et al. Dec. 2002; Oak Ridge National Laboratory: ORNL/SUB-02-19SXY162C/01 pp. 1-69.*

* cited by examiner

*Primary Examiner* — Russell Kallis
(74) *Attorney, Agent, or Firm* — Fellers, Snider, Blankenship, Bailey & Tippens, P.C.

(57) ABSTRACT

A new cultivar of switchgrass 'Cimarron' (SL93 2001-1) having increased biomass yield is provided. The switchgrass comprises all the morphological and physiological properties of the cultivar grown from a seed deposited under American Type Culture Collection (ATCC) No. PTA-10116. The invention also provides seeds, progeny, parts and methods of use of Cimarron, such as for the production of biofuels.

7 Claims, 2 Drawing Sheets

SWITCHGRASS CULTIVAR

CROSS-REFERENCE TO RELATED APPLICATIONS

This application claims benefit of U.S. provisional patent application 61/053,530, filed May 15, 2008, the complete contents of which is hereby incorporated by reference.

STATEMENT REGARDING FEDERALLY SPONSORED RESEARCH OR DEVELOPMENT

This invention was made with U.S. Government support under USDA/CSREES Grant No. 2001-34447-10302, USDA/CSREES Grant No. 2002-34447-11908, USDA/CSREES Grant No. 2003-34447-13162, USDA/CSREES Grant No. 2004-34447-14487, USDA/CSREES Grant No. 2005-34447-15711, and USDA/CSREES Grant No. 2006-34447-16939 awarded by the Department of Agriculture and under Contract No. DE-AC05-84OR21400 and Contract No. DE-AC05-00OR22725 awarded by the Department of Energy. The Government has certain rights in this invention.

BACKGROUND OF THE INVENTION

1. Field of the Invention

The invention generally relates to a new cultivar of switchgrass having increased biomass yield. In particular, the invention provides a switchgrass cultivar 'Cimarron', which was tested under the experimental ID 'SL93 2001-1', comprising all the morphological and physiological properties of a grass plants grown from seed deposited under American Type Culture Collection (ATCC) No. PTA-10116 as well as seeds and progeny thereof.

2. Description of Related Art

*Panicum virgatum*, commonly known as switchgrass, is a perennial warm season grass native to North America. Switchgrass is one of the dominant species of the North American tallgrass prairies and can be found in remnant prairies, in native grass pastures, and naturalized along roadsides. Its uses include as ground cover for soil conservation and to control erosion; for forage and grazing; as game cover; as an ornamental grass; for hay and pasture and as a substitute for wheat straw in many applications, including livestock bedding, straw bale housing, and as a substrate for growing mushrooms; and more recently as a biomass crop for ethanol, fiber, electricity, and heat production.

Switchgrass is being intensively researched as a bioenergy crop because it is a native perennial warm season grass with the ability to produce moderate to high yields on marginal farmlands. It is now being considered for use in several bioenergy conversion processes, including cellulosic ethanol production, biogas, and direct combustion for thermal energy applications. The main agronomic advantages of switchgrass as a bioenergy crop are its stand longevity, drought and flooding tolerance, relatively low herbicide and fertilizer input requirements, ease of management, hardiness in poor soil and climate conditions, and widespread adaptability in temperate climates. In addition, the energy inputs required to grow switchgrass are favorable when compared with annual seed bearing crops such as corn, soybean, or canola, which can require relatively high energy inputs for field operations, crop drying, and fertilization.

There is an ongoing need to discover or develop new varieties of switchgrass with favorable attributes, such as high biomass yield.

SUMMARY OF THE INVENTION

The present invention provides a new synthetic switchgrass cultivar Cimarron (SL93 2001-1) (*Panicum virgatum* L., lowland ecotype) produced from the random intercrossing of seven parent plants. Six of the parent plants of Cimarron (SL93 2001-1) originated from the 'SL93' breeding population, which was formed in 1993 by polycrossing approximately equal numbers (ca 300) of randomly chosen plants of 'Alamo' and 'PMT 279'. The new cultivar is characterized by a greater biomass yield, compared to other varieties of switchgrass, or to the parent varieties from which it was developed. FIG. 1 is a photograph of this new plant cultivar.

The invention provides a switchgrass cultivar Cimarron (SL93 2001-1). The switchgrass plant comprises all the morphological and physiological properties of a grass plants grown from a seeds deposited under American Type Culture Collection (ATCC) No. PTA-10116. In one embodiment of the invention, the new switchgrass plants are is planted in a sward.

The invention further provides seeds of the switchgrass cultivar of claim 1. When germinated and grown, the seeds produce a switchgrass plants comprising all the morphological and physiological properties of the switchgrass cultivar grown from a seed sample deposited under American Type Culture Collection (ATCC) No. PTA-10116.

The invention further provides progeny of the switchgrass cultivar according to the invention. The progeny plants comprise all the morphological and physiological properties of the cultivar grown from a seed sample deposited under American Type Culture Collection (ATCC) No. PTA-10116. The progeny plants usually result from a outcrossing of the switchgrass plants of the invention (switchgrass plants of cultivar Cimarron). However, the invention also encompasses progeny and seeds that result from self-fertilization.

The invention further provides a vegetative sprigs or clones of the switchgrass cultivar Cimarron. In addition, the invention provides parts of the switchgrass cultivar, the part being, for example roots, stems, leaves, pollen and/or seeds.

The invention further provides a lignocellulosic feedstock for use in the production of biofuel such as ethanol. The feedstock comprises harvested switchgrass plants of cultivar Cimarron. The harvested switchgrass plants of cultivar Cimarron comprise all the morphological and physiological properties of the cultivar grown from a seed sample deposited under American Type Culture Collection (ATCC) No. PTA-10116.

The invention further provides a method of producing biofuel ethanol. The method comprises the steps of 1) providing a lignocellulosic feedstock comprising harvested switchgrass plants of cultivar Cimarron; and 2) converting the lignocellulosic feedstock to biofuel ethanol, e.g. by fermentation of the feedstock by one or more microbes.

DETAILED DESCRIPTION

Figure 1:
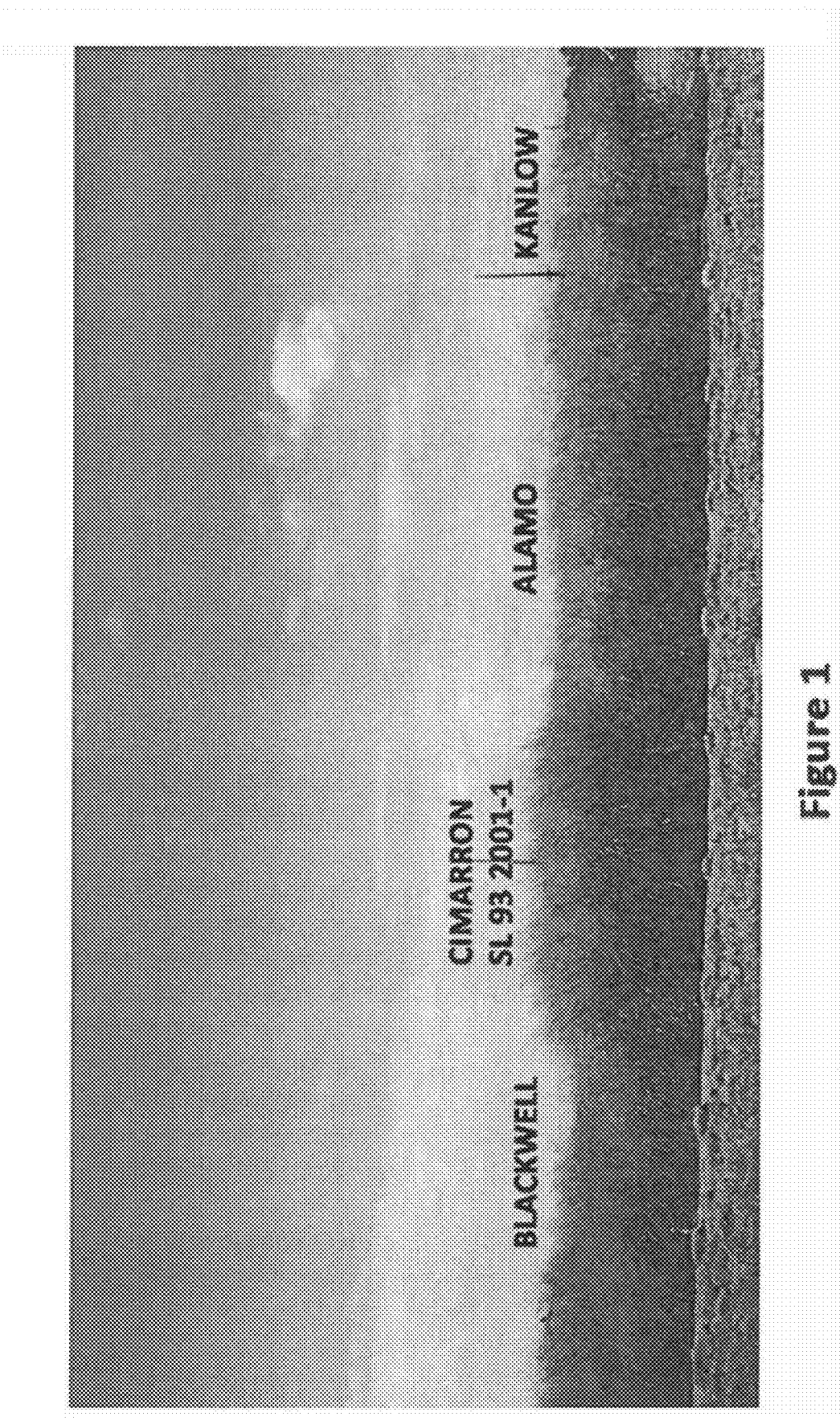
FIG. 1 is a photo of Cimarron (SL93 2001-1).

The present invention provides a new synthetic switchgrass cultivar (variety) Cimarron formerly tested as 'SL93 2001-1' (*Panicum virgatum* L., lowland ecotype) produced from the random intercrossing of seven parent plants. Compared to other varieties of switchgrass, including the parent plants from which the new cultivar was developed, Cimarron displays the advantages of a significantly enhanced biomass yield. The plant typically attains about 10 to 20 cm more in height than previously known varieties of switchgrass, which translates into a biomass yield that is from about 4 to about 10% or greater in biomass yield, compared to other types of switchgrass. Those of skill in the art will recognize that, depending on several factors such as planting conditions; competition for nutrients, sunlight, and water; temperature; soil type and condition; infection by pathogens; etc., individual plants produced from such seeds may differ somewhat from one another in appearance and properties. Thus, in one aspect, the invention provides a plant population whose mean characteristics for select traits (biomass yield, plant height, etc.) are as described herein and are reproducible across allowed generations (e.g. Breeder, Foundation, Registered, and Certified classes of Pedigree seed). References herein to "plant" or "seed" should be understood to encompass the plural (i.e. "plants" or "seeds") as the usual practice is to propagate, produce, and germinate, etc., a plurality of the switchgrass plants and/or seeds of cultivar Cimarron.

Six of the parent plants of Cimarron originated from the 'SL93' breeding population, which was formed in 1993 by polycrossing approximately equal numbers (ca 300) of randomly chosen plants of 'Alamo' and 'PMT 279'. Alamo is a lowland ecotype switchgrass, commercial cultivar, released in 1978. PMT 279 is a lowland ecotype switchgrass obtained from the National Resources Conservation Service (NRCS) Plant Materials Center, Knox City, Tex. During the years 1994-2000, three cycles of recurrent selection for increased biomass yield were completed in the SL93 population. Restricted Recurrent Phenotypic Selection (RRPS) was used for cycles 1 and 2, while Recurrent Selection for General Combining Ability (RSGCA) was used for cycle 3. The six parent plants (5-16, 6-8, 10-13, 10-30, 12-19, 16-27, and 22-28) were from the RSGCA C1 selection nursery, established in 1997 on the Stillwater Agronomy Farm. They were identified as plants with high general combining ability based on the performance of their half-sib progenies in biomass yield tests conducted in 1998-1999. The seventh parent plant, SU93 12-19, is one of many lowland plants found as contaminants in an upland population (SU93) formed in 1993. The lowland plants were probably Alamo from seed mislabeled by the source company as Blackwell. Subsequent half-sib progeny tests of several of the lowland contaminant plants identified SU93 12-19 as having superior general combining ability in biomass yield. Clonal plants of each of the seven parents were planted in an isolated replicated (7 replications) polycross nursery in spring 2001 at Lake Carl Blackwell. Syn-1 generation seed from this planting has been used to evaluate the cultivar.

Cimarron switchgrass plants have the general morphology and growth characteristics of Alamo switchgrass, but are larger. Plants are polymorphic, but generally robust, tall-growing, and have leaves and culms distinctly larger than upland ecotype cultivars like Blackwell. Like Alamo, plant color tends to be blue-green with some variation among plants in shading color. Plants of SL93 2001-1 are approximately 10 to 20 cm taller than Alamo when the inflorescence is mature. Color of spikelet and floret bracts (glumes, paleae, lemmas) is purple, less variable than those of Alamo. Plants tend to be slightly waxy. Leaves are rarely hairy on top near the base. The flowering time is similar to Alamo, later than Kanlow, which is 4 to 6 weeks later than in Blackwell. Seed are smooth and shiny, with about 426,000 per pound. Cimarron is a tetraploid with 2n=4x=36 chromosomes.

At least 2500 seeds of the switchgrass cultivar Cimarron were deposited with the American Type Culture Collection (ATCC, Manassas, Va.; ATCC Deposit No. PTA-10116) on Jun. 11, 2009 under the Budapest Treaty. The deposit is intended to meet all of the requirements of 37 C.F.R. §1.801-1.809. These seeds will be irrevocably and without restriction released to the public upon the issuance of a patent on Cimarron. The deposit will be maintained in the depository for a period of 30 years, or 5 years after the last request, or for the effective life of the patent, whichever is longer, and will be replaced if necessary during that period.

In one embodiment, the invention provides seeds of the switchgrass cultivar Cimarron. The seeds may be from the deposit ATCC No: PTA-10116 or may be from plants grown from seeds from ATCC Deposit No. PTA-10116, or from the progeny of such plants. When used in the practice of the invention, the seeds may be of individual genotypes of switchgrass Cimarron. Alternatively, the Cimarron seeds, when used as described herein, may be present in a mixture of seeds, e.g. mixed with seeds of another switchgrass cultivar, or seeds of another grass type altogether, according to the desired outcome of making the mixture, e.g. to provide a variety of types of grass in a field or meadow.

Cimarron seeds, and methods of producing Cimarron seeds (e.g. by growing Cimarron switchgrass plants, allowing the seeds to set, and harvesting the seeds) are also encompassed by the invention. The method involves planting Cimarron switchgrass as described herein under conditions that result in germination of Cimarron switchgrass seed, growth of Cimarron switchgrass plants and setting of progeny seeds, and harvesting the progeny seeds. Likewise, a method of producing Cimarron switchgrass plants is provided. The method involves propagating Cimarron switchgrass by planting or otherwise germinating Cimarron seeds as described herein under conditions that allow the germinated seed to develop into a plant.

In other embodiments, the invention provides Cimarron switchgrass plants having all the morphological and physiological characteristics of the cultivar from seed deposited as ATCC No: PTA-10116. The switchgrass plants may, in fact, have been grown from such seeds, or may be the progeny of such plants produced either from seed or by some other mode of propagation, e.g. vegetatively through rhizomes or/and tillers, or by using tissue culture techniques for clonal reproduction of parent plants. Tissue culture techniques may involve using explant sources such as anthers, young inflorescences, or other meristematic tissues of donor plants, etc. In each case, the resulting switchgrass has all the morphological and physiological characteristics of plants grown from seed deposited as ATCC No: PTA-10116. The invention thus also includes methods of producing or propagating Cimarron switchgrass plants using any of these methodologies.

The invention also includes switchgrass plants that are produced by crossing (either mechanically or by natural means) Cimarron with other non-isogenic grass varieties (outcrossing). Seeds and plants generated from those seeds that are the result of a first out-crossing are referred to as the F1 generation (first generation) and are encompassed by the present invention. Any grass capable of outcrossing with Cimarron can be used to create such outcrossed plants, and the invention provides methods of carrying out such crosses, and well as seeds and plants so produced.

The invention also includes switchgrass plants that are produced by self-fertilization ("selfing") either mechanically or by natural means, although this may be a rare occurrence, since crossing among different plants in the breeding population being the predominant mode of reproduction. Self-fertilization as used herein refers to the process of allowing the same switchgrass plant to pollinate itself, or letting one Cimarron plant pollinates another Cimarron switchgrass plant. The invention provides methods of performing such crosses, and seeds and plants so produced. Pollinations (either by selfing or outcrossing) are carried out by planting Cimarron switchgrass plants in close proximity to each other or another plant of interest (e.g. in an environment such as a field, or a controlled environment such as a test field or greenhouse) under conditions where pollination between plants occurs naturally, e.g. via wind, insects, etc. Alternatively, human- or person-implemented mechanical means may be employed to remove or collect pollen from one plant and transfer the collected pollen to one or more plants.

The invention also encompasses all parts of switchgrass plants that possess all the morphological and physiological characteristics of plants grown from seed deposited as ATCC No: PTA-10116. Such plant parts include but are not necessarily limited to the stem or culm, inflorescence, spikelets, anthers, embryos, ligule, auricle leaf, and roots, as well as plant parts that are associated with the plant life cycle such as seeds, buds, shoots, vegetative sprigs, clones, seedlings, crowns, rhizomes, etc. Further, the invention also encompasses cells and various subcellular components of the switchgrass Cimarron. In particular, the invention encompasses nucleic acids (DNA, RNA etc.) and proteins encoded thereby, of Cimarron switchgrass plants having all the morphological and physiological characteristics of the cultivar grown from seed deposited as ATCC No: PTA-10116. Further included are plant cells (either in the plant or in tissue culture), plant protoplasts, plant calli, plant clumps, pollen, etc.

In addition, various products produced from the switchgrass cultivar Cimarron are also encompassed by the invention, such products including but not limited to seeds, sod, harvested switchgrass, hay or other animal feed, bedding, dried biomass, cellulosic fibers produced from the plant, compressed pellets, lignocellulosic feedstock, round or square bales, baskets and other woven items, various fibers, etc.

Figure 2:
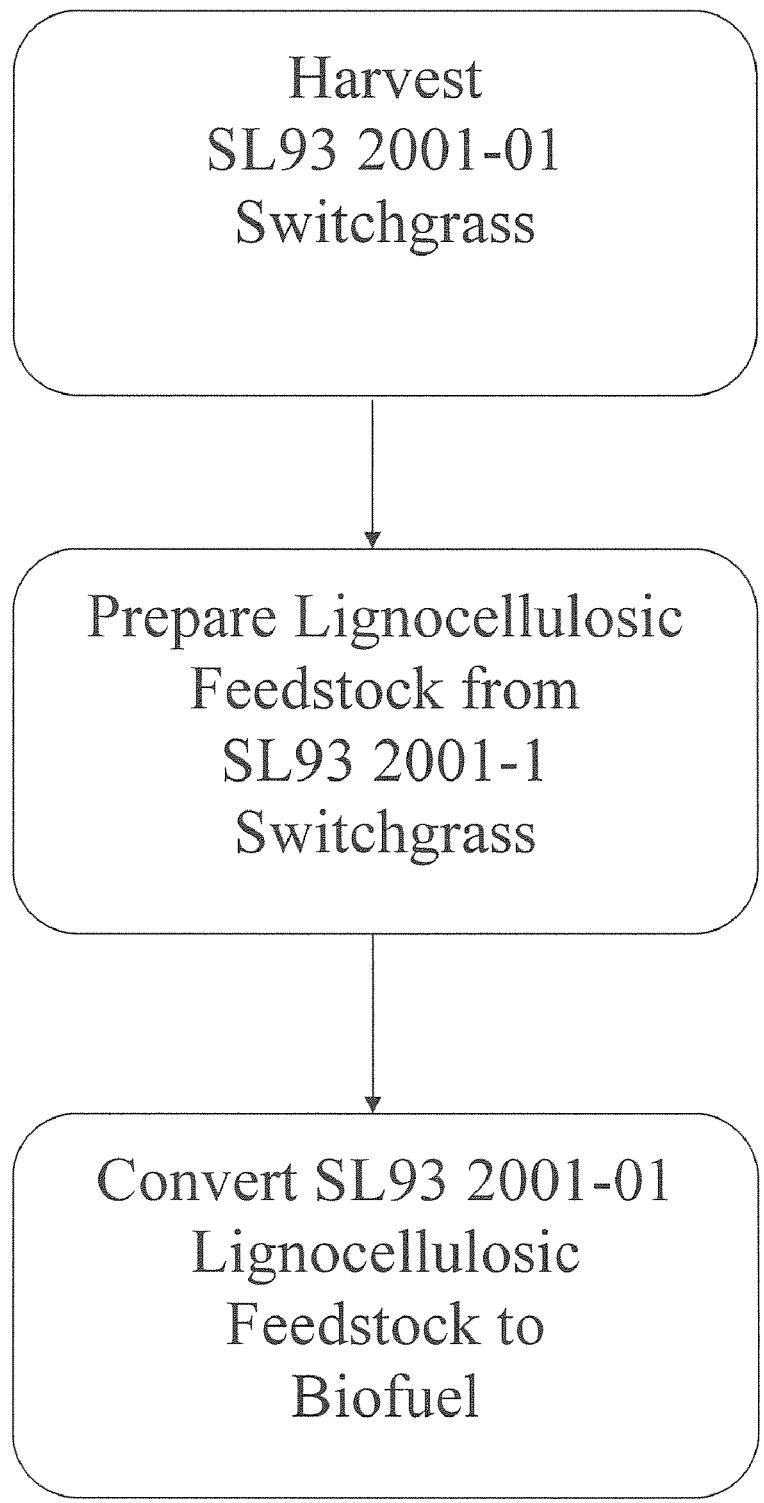
FIG. 2 is a schematic representation of producing biofuel using the switchgrass of the invention.

One significant potential use of Cimarron is as a bioenergy feedstock crop. Developing the technology to convert lignocellulosic feedstock to e.g. ethanol and other products on a commercially viable scale is currently an international high priority research goal. In particular, considerable effort is presently being expended in developing switchgrass as a cellulosic ethanol crop, and Cimarron, with its high biomass yields, is an excellent candidate for use in this manner. The invention therefore also includes methods of preparing biofuels such as ethanol, as illustrated schematically in FIG. 2. The methods include the steps of growing and harvesting Cimarron switchgrass plants of the invention, providing Cimarron switchgrass lignocellulosic feedstock (by preparing the feedstock using harvested Cimarron switchgrass), and converting Cimarron lignocellulosic feedstock into biofuels such as ethanol. The method thus typically involves switchgrass harvesting, transport, feedstock production, feedstock handling, and conversion. Various conversion technologies are available or in the process of being developed. Typically, conversion technologies include the action of a microbe (e.g. yeast, bacteria, fungi, oomycetes, etc.) e.g. by fermentation or other microbial metabolic or catabolic processes.

In addition, various thermal energy applications for switchgrass exist. For example, switchgrass can be pressed into fuel pellets that are subsequently burned in pellet stoves used to heat homes (which typically burn corn or wood pellets). Switchgrass can serve as a substitute for coal in power generation, for example, switchgrass (either alone or in combination with wood residues) may be used as feedstocks for pellets used for the firing of power plants that are otherwise coal-fired, or other heating applications, e.g. as a boiler fuel. Switchgrass, especially when pelletized and used as a solid biofuel, is thus an excellent candidate for displacing fossil fuels.

Additional anticipated uses of Cimarron also include traditional uses for lowland switchgrass cultivars, including but not limited to monoculture plantings for soil conservation, and for wildlife and livestock grazing and haying. Switchgrass is also frequently included as a component of native grass seed mixes for revegetation purposes. As such, the switchgrass of the invention may be present in any of several different forms, including but not limited to, planted in a sward, field, meadow, pasture, park, riparian area, or as a landscaping element, etc., and the present invention also encompasses such areas in which the switchgrass of the invention is planted, e.g. sod in which Cimarron is planted.

The invention also includes various recombinant, genetically engineered forms of the switchgrass plants of Cimarron. For example, the switchgrass may be genetically engineered (e.g. transformed) by methods that are known in the art to contain and express a gene encoding for resistance to a pathogen, or to drought or other untoward growth conditions. Known methods of introducing nucleic acids into plants or plant cells include, for example, microprojectile bombardment and *Agrobacterium*-mediated techniques. These and other techniques are described, for example, in: U.S. Pat. No. 7,511,205 to Mobel, Jr., (Mar. 31, 2009); U.S. Pat. No. 7,525,028 to Jenkinson (Apr. 28, 2009); U.S. Pat. No. 6,677,507 to de Bruijn (Jan. 13, 2004); and U.S. Pat. No. 6,407,319 to Rose-Fricker et al., (Jun. 18, 2002); the complete contents of each of which is hereby incorporated by reference in entirety.

The following Examples are intended to illustrate the invention but should not be construed so as to limit the scope thereof in any way.

EXAMPLES

Example 1

Fall Color Retention and Growth

Fall color retention and growth of Cimarron is similar to Alamo and greater than Kanlow, Blackwell, and Cave-in-Rock (Table 1).

TABLE 1

Fall dormancy ratings for switchgrass cultivars in Test 2006-1, Agronomy Research Station, Stillwater, OK. Nov. 11, 2007.

| | Rep | | | | |
|---|---|---|---|---|---|
| | 1 | 2 | 3 | 4 | |
| Cultivar | | Rating | | | Mean |
| NL 93-2 | 2 | 1 | 1 | 1 | 1.25 |
| Cimarron (SL93 2001-1) | 5 | 5 | 4 | 5 | 4.75 |
| NSL 2001-1 | 4 | 4 | 4 | 4 | 4.00 |
| NL94 2001-1 | 4 | 4 | 3 | 4 | 3.75 |
| Alamo 4 | 4 | 4 | 4 | 4 | 4.00 |
| Kanlow | 1 | 2 | 1 | 1 | 1.25 |
| NSU95 2001-1 | 2 | 2 | 2 | 2 | 2.00 |
| Blackwell | 1 | 1 | 1 | 1 | 1.00 |
| Cave-in-Rock | 3 | 2 | 2 | 2 | 2.25 |

Scale:
1 = fully brown,
2 = 80-90% brown,
3 = 50-79% brown,
4 = 50-79% green,
5 = fully green.

Example 2

Performance

Biomass Yield: Biomass yields of Cimarron and standard cultivars have been compared in one test at the Cimarron Valley Research Station (CVRS), Perkins, Okla. and three tests at the Agronomy Research Station (ARS), Stillwater, Okla. (Tables 2-5). Tests 2002-1 (CVRS, Table 2) and 2002-2 (ARS, Table 3), established in 2002, compared Cimarron, Kanlow, Alamo and other experimental strains from 2003 through 2005. Tests 2006-1 (ARS, Table 4) and 2006-2 (ARS, Table 5) established in 2006, compared SL93 2001-1, Alamo, Kanlow, and other standard and experimental cultivars in 2007. Biomass yield data from all tests are from one harvest near the end of each growing season.

Biomass yields of Cimarron were numerically and consistently higher than Alamo, the best check performer, by 4.2-12.1% in all trials and by 4.3-9.1% over all years, though yield differences were often not statistically significant as indicated by the LSD tests. Yield of Cimarron was significantly greater than Alamo in Test 2002-2 (CVRS) for the 3-year mean (P<0.05) (Table 3). Cimarron also had significantly (<0.10) higher yield than Alamo in Test 2006-2 in 2007 (Table 5). When analyzed over all environments (locations and years), Cimarron had a mean annual biomass yield (16.06 tons/ha) 1.12 tons/ha greater than Alamo (14.94 tons/ha), which was significant (P=0.0049) (Table 6). Biomass yields of Cimarron were significantly greater than those of Kanlow in all environments (<0.05) (Tables 2-5). Analyzed over environments, the mean biomass yield of Cimarron (16.06 tons/ha) exceeded that of Kanlow (12.89 tons/ha) by 3.17 tons/ha (P=0.0001) (Table 6). Biomass yields of SL93 2001-1, Alamo, and usually Kanlow were substantially and significantly greater than those of upland cultivars in Tests 2006-1 and 2006-2.

TABLE 2

Biomass yields (tons dry matter/ha) of commercial and experimental switchgrass cultivars in Test 2002-1, Agronomy Research Station, Stillwater, OK, 2003-2005.

| Cultivar | Harvest Year | | | |
|---|---|---|---|---|
| | 2003 | 2004 | 2005 | 3-yr Mean |
| Alamo | 13.79 | 15.43 | 11.83 | 13.69 |
| Kanlow | 10.74 | 13.39 | 10.11 | 11.41 |
| SL93 10-13 | 14.03 | 17.29 | 14.33 | 15.22 |
| NSL 2001-3 | 15.69 | 16.46 | 12.71 | 14.96 |
| NSL 2001-10 | 15.86 | 16.47 | 12.15 | 14.83 |
| SL93 2001-2 | 15.70 | 16.07 | 11.63 | 14.47 |
| Cimarron (SL93 2001-1) | 14.86 | 16.39 | 12.04 | 14.43 |
| SL93 2001-6 | 14.38 | 16.39 | 12.38 | 14.39 |
| SL93 5-16 | 15.05 | 15.83 | 10.92 | 13.93 |
| NSL 2001-6 | 14.24 | 15.79 | 11.72 | 13.91 |
| SL93 6-8 | 13.62 | 15.98 | 12.02 | 13.87 |
| NSL 2001-13 | 12.95 | 15.50 | 12.67 | 13.70 |
| NSL 2001-1 | 13.85 | 15.71 | 11.13 | 13.56 |
| SL93 2001-5 | 13.69 | 15.72 | 11.15 | 13.52 |
| NL94 2001-1 | 14.03 | 15.81 | 10.53 | 13.46 |
| NSL 2001-11 | 13.60 | 15.49 | 11.14 | 13.41 |
| NL94 18-24 | 15.21 | 14.91 | 9.91 | 13.34 |
| SL93 2001-4 | 13.19 | 15.48 | 11.21 | 13.30 |
| NSL 2001-7 | 13.38 | 15.17 | 11.27 | 13.27 |
| SU93 12-19 | 12.85 | 15.16 | 11.79 | 13.26 |
| NSL 2001-5 | 13.27 | 15.41 | 11.04 | 13.24 |
| NL94 28-22 | 13.52 | 14.85 | 10.92 | 13.10 |
| SYN NL94-1 | 13.44 | 14.96 | 10.78 | 13.06 |
| NSL 2001-9 | 13.08 | 15.19 | 10.51 | 12.93 |
| NL94 2001-4 | 14.04 | 13.96 | 10.51 | 12.84 |
| NSL 2001-2 | 13.65 | 13.98 | 10.44 | 12.69 |
| SYN SL94-1 | 13.19 | 14.17 | 10.39 | 12.58 |
| NL94 27-23 | 12.31 | 14.05 | 11.14 | 12.50 |
| SYN SL93-3 | 13.13 | 14.17 | 9.58 | 12.29 |
| NSL 2001-4 | 12.38 | 13.77 | 9.63 | 11.93 |
| NL94 2001-3 | 12.05 | 13.15 | 9.68 | 11.63 |
| NL94 2001-2 | 12.68 | 12.98 | 8.92 | 11.53 |
| NSL 2001-12 | 11.39 | 12.81 | 9.28 | 11.16 |
| NSL 2001-8 | 11.73 | 12.92 | 8.33 | 10.99 |
| SL93 2001-3 | 12.20 | 11.84 | 8.69 | 10.91 |
| SL93 2001-7 | 10.76 | 11.51 | 9.28 | 10.51 |
| Mean | 13.43 | 14.84 | 10.88 | 13.05 |
| 5% LSD | 1.62 | 1.95 | 1.72 | 1.03 |
| 10% LSD | 1.36 | 1.63 | 1.44 | 0.87 |

TABLE 3

Biomass yields (tons dry matter/ha) of commercial and experimental switchgrass cultivars in Test 2002-2, Cimarron Valley Research Station, Perkins, OK, 2003-2005.

| Cultivar | Harvest Year | | | |
|---|---|---|---|---|
| | 2003 | 2004 | 2005 | |
| Alamo | 13.29 | 12.89 | 14.05 | 13.41 |
| Kanlow | 11.25 | 11.54 | 12.78 | 11.86 |
| SL93 5-16 | 16.68 | 17.38 | 16.90 | 16.99 |
| SL93 6-8 | 16.16 | 16.90 | 17.41 | 16.82 |
| SL93 10-13 | 15.67 | 16.82 | 16.56 | 16.35 |
| SL93 2001-2 | 15.51 | 16.33 | 16.63 | 16.16 |
| SU93 12-19 | 15.72 | 16.85 | 15.78 | 16.12 |
| NSL 2001-10 | 15.88 | 16.06 | 15.41 | 15.79 |
| NSL 2001-3 | 15.45 | 15.53 | 15.95 | 15.64 |
| SL93 2001-6 | 15.03 | 15.82 | 15.60 | 15.48 |
| NL94 18-24 | 16.33 | 14.73 | 14.11 | 15.06 |
| NSL 2001-5 | 15.07 | 14.66 | 14.80 | 14.84 |
| Cimarron (SL93 2001-1) | 14.67 | 14.51 | 14.93 | 14.71 |
| NSL 2001-2 | 15.41 | 14.15 | 14.72 | 14.66 |
| NSL 2001-11 | 14.41 | 14.14 | 14.85 | 14.47 |
| SL93 2001-3 | 14.77 | 14.03 | 14.48 | 14.43 |
| NSL 2001-1 | 14.55 | 14.93 | 13.68 | 14.39 |
| NL94 28-22 | 14.37 | 13.86 | 14.83 | 14.35 |
| SL93 2001-4 | 14.00 | 14.53 | 14.48 | 14.34 |
| NL94 27-23 | 14.11 | 13.73 | 14.59 | 14.14 |
| SL93 2001-5 | 13.71 | 14.28 | 14.01 | 14.00 |
| SYN SL93-3 | 13.75 | 13.88 | 13.73 | 13.79 |
| NSL 2001-4 | 14.75 | 13.13 | 13.37 | 13.75 |
| NSL 2001-9 | 14.05 | 14.16 | 13.00 | 13.74 |
| NSL 2001-6 | 12.79 | 12.73 | 13.18 | 12.90 |
| NSL 2001-7 | 12.20 | 13.20 | 12.83 | 12.74 |
| NL94 2001-1 | 10.85 | 13.29 | 13.82 | 12.65 |
| NSL 2001-13 | 12.32 | 11.96 | 13.27 | 12.52 |
| NSL 2001-12 | 13.26 | 11.81 | 12.24 | 12.44 |
| NSL 2001-8 | 12.62 | 12.21 | 11.67 | 12.17 |
| NL94 2001-4 | 12.22 | 11.64 | 12.40 | 12.09 |
| SL93 2001-7 | 11.57 | 11.79 | 11.72 | 11.69 |
| SYN SL94-1 | 10.89 | 8.71 | 11.67 | 11.54 |
| NL94 2001-2 | 10.92 | 11.28 | 1.44 | 11.21 |
| NL94 2001-3 | 8.58 | 11.00 | 11.32 | 10.30 |
| SYN NL94-1 | 5.66 | 12.06 | 10.32 | 8.23 |
| Mean | 13.57 | 13.79 | 13.95 | 13.77 |
| 5% LSD | 1.84 | 1.98 | 2.24 | 1.17 |
| 10% LSD | 1.54 | 1.66 | 1.88 | 0.98 |

TABLE 4

Biomass yields (tons dry matter/ha) of commercial and
experimental switchgrass cultivars in NF-OSU Switchgrass
Test 2006-1, Cow Creek Bottom, Stillwater, OK, 2007.

|   | Cultivar | Biomass yield (ton/ha) | Percentage of Alamo | Percentage of Kanlow |
|---|---|---|---|---|
| 1 | Cimarron (SL 93 2001-1) | 15.52 | 104.23 | 127.63 |
| 2 | Alamo | 14.89 | 100.00 | 122.45 |
| 3 | NSL 2001-1 | 14.16 | 95.10 | 116.45 |
| 4 | Kanlow | 12.16 | 81.67 | 100.00 |
| 5 | Shawnee | 10.69 | 71.79 | 87.91 |
| 6 | Cave-In-Rock | 10.50 | 70.52 | 86.35 |
| 7 | Trailblazer | 8.81 | 59.17 | 72.45 |
| Mean | | 13.20 | | |
| CV (%) | | 16.63 | | |
| 5% LSD | | 2.54 | | |
| 10% LSD | | 2.12 | | |

TABLE 5

Biomass yields (tons dry matter/ha) of commercial and experimental
switchgrass cultivars in OSU Switchgrass Test 2006-2, Agronomy
Research Station, Stillwater, OK, 2007.

| | Entry | Biomass yield (ton/ha) | Percentage of Alamo | Percentage of Kanlow |
|---|---|---|---|---|
| | Cimarron (SL 93-2001-1) | 26.06 | 112.13 | 124.09 |
| | NSL 2001-1 | 24.27 | 104.43 | 115.57 |
| | NL 93-2 | 24.09 | 103.66 | 114.71 |
| | Alamo | 23.24 | 100.00 | 110.67 |
| | NL 94-2001-1 | 22.75 | 97.89 | 108.33 |
| | Kanlow | 21.00 | 90.36 | 100.00 |
| | NSU 95-2001-1 | 12.09 | 52.02 | 57.57 |
| | Blackwell | 11.25 | 48.41 | 53.57 |
| | Cave-in-Rock | 11.61 | 49.96 | 55.29 |
| Mean | | 19.60 | | |
| CV (%) | | 11.23 | | |
| 5% LSD | | 3.21 | | |
| 10% LSD | | 2.66 | | |

TABLE 6

Biomass yields (tons dry matter/ha) of two experimental and two best
commercial switchgrass cultivars and their comparisons across four field
tests (Test 2002-1, Test 2002-2, NF-OSU Switchgrass 2006-1, and OSU
Switchgrass 2006-2) over four years (2003, 2004, 2005, and 2007).

| Cultivar | Biomass Yield† (tons/ha) | Biomass Yield Advantage (tons/ha) and Significance Level | | |
|---|---|---|---|---|
| | | NSL 2001-1 | Alamo | Kanlow |
| Cimarron (SL 93 2001-1) | 16.06 | 0.80 P = 0.0870 | 1.12 P = 0.0049 | 3.17 P < 0.0001 |
| NSL 2001-1 | 15.26 | — | 0.33 P = 0.3710 | 2.38 P < 0.0001 |
| Alamo | 14.94 | — | — | 2.05 P < 0.0001 |
| Kanlow | 12.89 | — | — | — |

†indicating least squares means over all tests and years, which were calculated by SAS Proc Mixed model using Cultivar as fixed effect and Test, Year, Replication as random effects.

Example 3

Forage Quality

While data have not been collected on forage quality of Cimarron, but, because there was no selection for forage quality indices or traits correlated with forage quality, the forage quality of Cimarron is similar to Alamo.

Example 4

Pests

No unusual pest problems have been observed in plantings of Cimarron. Like Alamo and Kanlow, Cimarron has greater resistance to leaf spotting diseases than upland ecotype switchgrass cultivars. Occasional plants have yellow coloration indicative of infection by *Panicum* mosaic virus.

Example 5

Geographic Adaptation

While Cimarron has not been tested over a geographic range sufficiently large to provide definitive information on its adaptation boundaries, it was developed from a population formed from Alamo and PMT 279 (similar geographic origin and adaptation), which suggests that it should have a similar range of adaptation, i.e. it should be well adapted throughout the southern US to approximately 38 degrees North latitude. The delayed fall dormancy of Cimarron relative to Kanlow is possibly indicative of somewhat lesser winter hardiness. However, there has been no indication of that possibility in the field plantings used in its testing. There has been no winter injury to Cimarron throughout its breeding and testing in Stillwater Okla. and vicinity.

We claim:

1. A switchgrass cultivar Cimarron, comprising all the morphological and physiological properties of the cultivar grown from a seed deposited under American Type Culture Collection (ATCC) No. PTA-10116.

2. The switchgrass cultivar of claim 1 planted in a sward.

3. Seed of the switchgrass cultivar of claim 1, wherein said seed produces a switchgrass plants comprising all the morphological and physiological properties of the cultivar grown from a seed deposited under American Type Culture Collection (ATCC) No. PTA-10116.

4. Progeny of switchgrass cultivar Cimarron according to claim 1, wherein said progeny comprise all the morphological and physiological properties of the cultivar grown from a seed deposited under American Type Culture Collection (ATCC) No. PTA-10116.

5. The progeny of claim 4, wherein said progeny result from outcrossing of the switchgrass cultivar plants of claim 1.

6. A vegetative sprig or clone of the switchgrass cultivar of claim 1.

7. A part of the switchgrass cultivar plant of claim 1, wherein said part is selected from the group consisting of roots, stems, leaves, pollen and seeds.

* * * * *